US006569619B1

(12) United States Patent
Sivaraja

(10) Patent No.: US 6,569,619 B1
(45) Date of Patent: *May 27, 2003

(54) HIGH-THROUGHPUT IN VITRO SCREENING ASSAYS FOR MODULATORS OF NUCLEIC ACID HELICASES

(75) Inventor: Mohanram Sivaraja, Palo Alto, CA (US)

(73) Assignee: Tularik, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/124,312

(22) Filed: Jul. 29, 1998

(51) Int. Cl.[7] .................................................. C12G 1/68
(52) U.S. Cl. ............................ 435/6; 435/7.1; 435/18; 435/195
(58) Field of Search .............................. 435/6, 7.1, 18, 435/195

(56) References Cited

U.S. PATENT DOCUMENTS

| 4,203,848 | A |   | 5/1980  | Grandine, II ............... 210/490 |
|-----------|---|---|---------|--------------------------------------|
| 5,217,864 | A |   | 6/1993  | Heintz et al. ................... 435/6 |
| 5,273,881 | A |   | 12/1993 | Sena et al. ...................... 425/6 |
| 5,705,344 | A | * | 1/1998  | Giordano et al. .............. 435/6 |
| 5,747,247 | A | * | 5/1998  | Kowalczykowski et al. ... 435/6 |
| 5,958,696 | A | * | 9/1999  | Crute ............................. 435/6 |

FOREIGN PATENT DOCUMENTS

| GB | 2311068   | 9/1997  |
|----|-----------|---------|
| WO | WO 97/36006 | 10/1997 |

OTHER PUBLICATIONS

Bachur, et al., "Helicase Inhibition by Anthracycline Anti-cancer Angents," *Molecular Pharmacology*, 41:993–998 (1992).
Crute, et al., "Inhibition of Herpes Simplex Virus Type 1 Helicase—Primase by (Dichloroanilino) purines and –pyrimidines," *J. Med. Chem.*, 38(10):1820–1825.
Kyono, et al., "Detection of Hepatitis C Virus Helicase Activity Using the Scintillation Proximity Assay System," *Analytical Biochemistry*, 257:120–126.
Maine, et al., "The Antitumor Agent CC–1065 Inhibits Helicase–Catalyzed Unwinding of Duplex DNA+," *Biochemistry*, 31(16):3968–3975 (1992).
Naegeli, et al., "Inhibition of Rad3 DNA Helicase Activity by DNA Adducts and Abasic Sites: Implications for the Role of a DNA Helicase in Damage–Specific Incision of DNA+," *Biochemistry*, 32(2):613–621 (1993).
Matson, et al., "DNA Helicases," *Annu. Rev. Biochemistry*, 59:289–329 (1990).
Seki, et al., "DNA Helicase and Nucleoside–5'–triphosphatase Activities of Polyoma Virus Large Tumor Antigen," *Biochemistry*, 29(4):1003–1009 (1990).
Tuteja, et al., "DNA helicase III from HeLa cells: an enzyme that acts preferentially on partially unwound DNA duplexes," 20(20):5329–5337 (1992).
Roman, et al., *Biochemistry*, 28:2863–2873 (1989).

\* cited by examiner

*Primary Examiner*—Nashaat T. Nashed
(74) *Attorney, Agent, or Firm*—Townsend & Townsend & Crew LLP

(57) ABSTRACT

The present invention provides solid phase assays for measuring helicase activity in the presence or absence of a potential helicase activity modulator. High throughput methods, compositions, kits and integrated systems are provided for detecting helicase activity in vitro and for measuring the effect of potential helicase activity modulators.

20 Claims, 1 Drawing Sheet

US 6,569,619 B1

HIGH-THROUGHPUT IN VITRO SCREENING ASSAYS FOR MODULATORS OF NUCLEIC ACID HELICASES

FIELD OF THE INVENTION

The present invention relates generally to high-throughput in vitro screening assays for identifying modulators of helicase activity. New solid phase assays, related compositions, apparatus and integrated systems are provided.

BACKGROUND OF THE INVENTION

The unwinding of duplex DNA is a prerequisite for DNA relication and repair, providing the single-stranded DNA (ssDNA) template for DNA polymerase to copy. Duplex DNA must also be unwound to generate the ssDNA required in recombination pathways or transferred during bacterial conjugation. A class of enzymes, the DNA helicase, enzymatically unwind DNA to facilitate this strand separation reaction. These enzymes are distinct from topoisomerases, which alter the linking number of the duplex DNA molecule through phosphodiester bond breakage and reunion. The helicases, on the other hand, simply disrupt the hydrogen bonds that hold the two strands of duplex DNA together. This is accomplished in a reaction that is coupled with the hydrolysis of a nucleoside 5'-triphosphate (NTP) and, thus, all helicases described to date are also DNA-dependent nucleoside 5'-triphosphatases (NTPases).

Examples of DNA helicase enzymes are now numerous in phage, bacteria, viruses, and in eukaryotic cells suggesting that these enzymes are ubiquitous in nature. Individual cells contain multiple DNA helicases; each helicase having a unique biochemical role in the cell. In fact, it is now known that helicases are involved in a wide variety of cellular functions, including DNA replication, recombination and repair, and RNA transcription, translation and processing. As a result of the critical functions played by helicases, they provide promising targets for therapeutic intervention, e.g., in pathogenic infection.

The standard assay currently used for measuring helicase activity employs gel electrophoresis to monitor the unwinding of double-stranded DNA or RNA. Because this assay is time-consuming and cumbersome, several additional types of assays for measuring helicase activity have been developed. Such assays involve measuring the sensitization of labeled duplex DNA to single-strand specific nucleases, electron microscopy, displacement of a labeled fragment that is annealed to a single-stranded DNA or RNA molecule and, more recently, spectrophotometric assays utilizing a dye or ssDNA binding protein as the reporter molecule (see, e.g., Matson, et al., *Annu. Rev. Biochem.*, 59:289–329 (1990); Houston and Kodadek, *Proc. Natl. Acad. Sci. USA*, 91:5471–6474 (1994); Raney, et al., *Proc. Natl. Acad. Sci. USA*, 91:6644–6648 (1994); and Roman and Kowalczykowski, *Biochemistry* 28: 2863–2873 (1989)).

Shortcomings associated with these previously used assays have hampered the search for novel modulators of helicase activity. For example, many of these assays are slow, expensive, and insensitive, subject to interference and/or require considerable manipulation. Moreover, these assays are not amenable to high-throughput screening methods such as are needed to screen large libraries or groups of potential modulators.

Giordano, et al. have recently developed a high-throughput screening assay for inhibitors of nucleic acid helicases that overcomes the shortcomings of the previously used assays (see, U.S. Pat. No. 5,705,344). In this assay, helicase activity is detected by the solid-phase, preferential capture of retained (non-liberated) single-stranded nucleic acid comprising a detectable label. Although this assay is invaluable, it would be advantageous to have additional high-throughput screening assays for identifying modulators of helicase activity. The present invention provides such assays.

SUMMARY OF THE INVENTION

High-throughput assays for identifying modulators of helicase activity are provided. Both inhibitors and activators of helicase activity can be screened using the assays of the present invention. Solid phase throughput assays are provided, as are related assay compositions, integrated systems for assay screening and other features that will be evident upon review.

In one aspect, high-throughput in vitro screening assays are provided for helicase activity. In one such assay, a reaction mixture comprising a first nucleic acid hybridized to a complementary unlabeled second nucleic acid, a helicase polypeptide and a nucleoside triphosphate is incubated under conditions suitable for the helicase polypeptide to unhybridize, i.e., unwind, the first nucleic acid and the second nucleic acid. An excess amount of a third nucleic acid comprising an immobilizable tag is added to the reaction mixture, the third nucleic acid having a region that is complementary to the first nucleic acid. The reaction mixture is incubated under conditions suitable for the third nucleic acid to hybridize to the first nucleic acid to form an immobilizable hybridization complex, whereby the immobilizable hybridization complex becomes immobilized on a solid suppot to which the immobilizable tag binds. The solid support is washed and, thereafter, the presence, absence or amount of the immobilizable hybridization complex bound to the solid support is determined directly or indirectly.

In a presently preferred embodiment, a potential modulator of helicase activity is also added to the reaction mixture and the effect of the modulator on the helicase activity is determined. As such, the present invention includes methods of screening for helicase activity by comparing candidate helicase activities with one or more defined control helicase activities or, alternatively, methods of screening for modulators of one or more defined helicase activities by comparing helicase activities in the presence and absence of a candidate modulator.

In another aspect, the present invention provides kits, compositions and integrated systems for performing the assays disclosed herein.

Other features objects and advantages of the invention and its preferred embodiments will become apparent from the detailed description that follows.

DETAILED DESCRIPTION OF THE INVENTION AND PREFERRED EMBODIMENTS

A. General Overview

Figure 1:
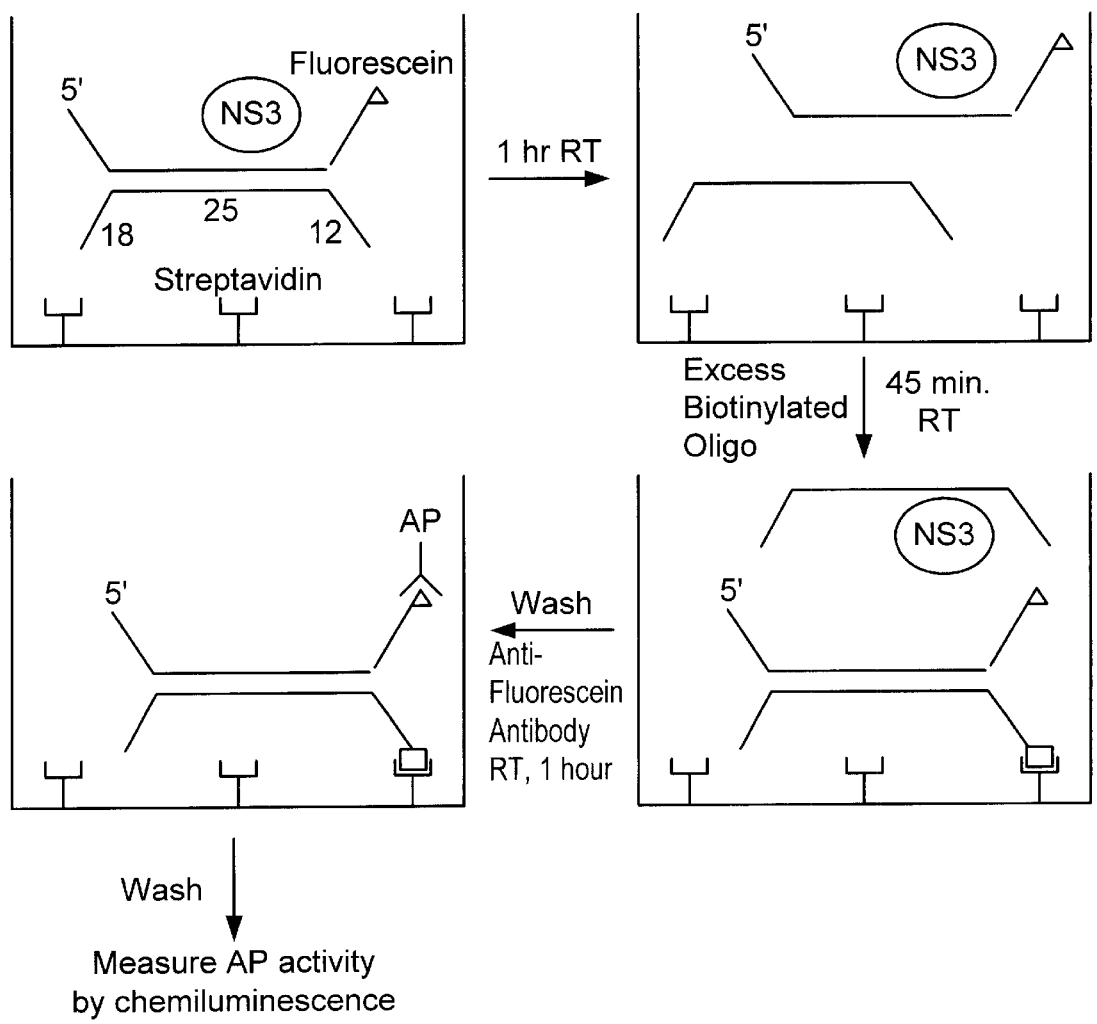
FIG. 1 illustrates a schematic of an automated helicase assay in accordance with the present invention (sequence= SEQ ID NO: 1).

The invention provides efficient assays and compositions for detecting helicase activity and for identifying specific modulators of helicase activity. The assays of the present invention are amenable to automated, cost-effective, high-throughput drug screening and, thus, have immediate application in a broad range of domestic and international pharmaceutical and biotechnology drug development programs. In addition, the present invention provides kits for screening for modulators of helicase activity, the kits including, for example, premeasured amounts of the various components used in the assays of the present invention.

The assays of the present invention have, inter alia, at least two immediately useful properties. First, the assays can be used to detect helicase activity in vitro. As such, the assays provide broadly applicable tools for assessing helicase activity in a high-throughput format. Such assays can be used as research tools to study the enzymology of helicases. Second, the assays provide for the identification of modulators of helicase activity. Such modulators are valuable research tools that can be used to elucidate the biochemistry and enzymology of, for example, DNA duplication and repair in both prokaryotic and eukaryotic systems. Moreover, such modulators provide lead compounds for drug development to treat a variety of conditions, including the development of the drugs useful for treating bacterial, fungal and viral infections, metabolic disease, genetic diseases, cell growth and regulatory dysfunctions, such as neoplasia, inflammation, hypersensitivity, etc. In addition, helicase modulators that specifically target undesired organisms, such as viruses, fungi, agricultural pests, or the like, can serve as fungicides, bactericides, herbicides, insecticides, etc. Accordingly, the assays of the present invention are of immediate value as a result of their ability to identify lead compounds for pharmaceutical and/or other research applications. Moreover, such assays are particularly well suited to high-throughput automation, making them especially valuable for their ability to identify lead compounds.

More particularly, the assays of the present invention have a number of advantages over existing assays. Such advantages include, but are not limited to, the following. First, there is no requirement that radioactive reagents be employed (although they are optionally used as discussed below). Second, the assays of the present invention can be performed in the solid-phase. Third, the signal generated using the assays is significantly larger and more robust than those typically obtained using previously known helicase assay methodologies. Fourth, other than the optionally employed immune detection reagents, there is no requirement to employ additional enzymatic components in the assay. Fifth, the assays can be run in a parallel fashion such that multiple different helicase enzymes are assayed simultaneously. Sixth, the assay format does not require that the helicase be immobilized on a solid support during the course of the assays. Seventh, the assays employ simple reagents that can be readily synthesized and obtained in the quantities needed for high-throughput screening in a modem drug discovery system. Finally, the assays of the present invention are readily amenable for automation and high-throughput screening ("HTS") using current reagents, devices and methodologies.

B. Helicases

The assays of the present invention are useful for determining the activity of many different helicases. Moreover, the assays of the present invention are useful for identifying modulators of many different helicases. Helicases are generally reviewed in, for example, Matson, et al., *Annu. Rev. Biochem.*, 59:289–329 (1990). In the assays of the present invention, preferred helicases are typically selected from medically relevant sources. As such, the helicases are generally pathogenic helicases, i.e., any helicase activity that is harmful to the host cell or organism). The particular helicase used in the assays of the present invention is selected based on the target application. For instance, rapidly growing cells (e.g., in neoplasia) can be targeted by inhibitors of human helicases, especially replicative helicases. In addition, pathogen-selective or pathogen-specific helicases can be used to identify therapeutic agents that are useful for the treatment of infectious disease. Fungal, viral, bacterial and parasitic helicases, in particular, provide medically urgent targets for identifying inhibitors using the assays of the present invention. In addition, a plurality of helicases or a panel comprising a preselected range of different helicases can be used to maximize the scope of the assays.

Preferred pathogenic helicases are derived from medically significant infectious organisms, including infections fungi, such as Aspergillus, Candida species; bacteria, such as Staphylococci (e.g., aureus), Streptococci (e.g., pneumoniae), Clostridia (e.g., perfringens), Neisseria (e.g., gonorrhoeae), Enterobacteriaceae (e.g., coli), Helicobacter (e.g., pylori), Vibrio (e.g., cholerae), Capylobacter (e.g., jejuni), Pseudomonas (e.g., aeruginosa), Haemophilus (e.g., influenzae), Bordetella (e.g., pertussis), Mycoplasma (e.g., pneumoniae), Ureaplasma (e.g., urealyticum), Legionella (e.g., pneumophila), Spirochetes (e.g., Treponema, Leptospira and Borrelia), Mycobacteria (e.g., tuberculosis and smegmatis), Actinomycies (e.g., israelii), Nocardia (e.g., asteroides), Chlamydia (e.g., trachomatis), Rickettsia, Coxiella, Ehrlichia, Rochalimaea, Brucella, Yersinia, Fracisella, and Pasteurella; protozoa, such as sporozoa (e.g., Plasmodia), rhizopods (e.g., Entamoeba) andflagellates (Trypanosoma, Leishmania, Trichomonas, Giardia, etc.); and viruses, such as (+) RNA viruses (such as Picomaviruses, e.g., polio; Togaviruses, e.g., rubella; Flaviviruses, e.g., HCV; and Coronaviruses), (−) RNA viruses (such as Rhabdoviruses, e.g., VSV; Paramyxoviruses, e.g., RSV; Orthomyxoviruses, e.g., influenza; Bunyaviruses and Arenaviruses), dsDNA viruses (e.g., Reoviruses), RNA to DNA viruses, i.e., Retroviruses, e.g., HIV, and certain DNA to RNA viruses, such as Hepatitis B virus. Other assays are designed to be relevant to non-medical uses, such as assays identifying inhibitors of helicases derived from crop pests, e.g., insects, fungi, weed plants, and the like.

The helicases used in the assays of the present invention can be purified from a natural source or can be recombinant, and are usually provided in at least a partially purified form. In one embodiment, the helicases are synthesized using recombinant DNA methodology. Generally, this involves creating a DNA sequence that encodes the helicase, modified as desired, placing the DNA in an expression cassette under the control of a particular promoter, expressing the protein in a host, isolating the expressed protein and, if required, renaturing the protein. Helicase nucleic acids that are useful for recombinant production of helicases for use in the assays of the invention, and methods of obtaining such nucleic acids, are known to those of skill in the art.

Helicase nucleic acids (e.g., cDNA, genomic, or subsequences (probes)) can be cloned, or amplified by in vitro methods, such as by the polymerase chain reaction (PCR), the ligase chain reaction (LCR), the transcription-based amplification system (TAS), the self-sustained sequence replication system (SSR). A wide variety of cloning and in vitro amplification methodologies are well known to persons of skill. Examples of these techniques and instructions sufficient to direct persons of skill through many cloning exercises are found in Berger and Kimmel, Guide to Molecular Cloning Techniques, Methods in Enzymology 152 Academic Press, Inc., San Diego, Calif. (Berger); Sambrook et al. (1989) Molecular Cloning—A Laboratory Manual (2nd ed.) Vol. 1–3, Cold Spring Harbor Laboratory, Cold Spring Harbor Press, NY, (Sambrook et al.); *Current Protocols in Molecular Biology, F. M. Ausubel et al., eds., Current Protocols, a joint venture between Greene Publishing Associates, Inc. and John Wiley & Sons, Inc.,* (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.,* 35: 1826; Landegren et al., (1988) *Science,* 241: 1077–1080; Van Brunt (1990) *Biotechnology,* 8: 291–294; Wu and Wallace, (1989) *Gene,* 4: 560; and Barringer et al. (1990) *Gene,* 89: 117.

DNA encoding the helicases can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066. In one preferred embodiment, a nucleic acid encoding a helicase can be isolated by routine cloning methods. A nucleotide sequence of a helicase gene as provided in, for example, GenBank or other sequence database can be used to provide probes that specifically hybridize to a helicase gene in a genomic DNA sample, or to a helicase MRNA in a total RNA sample (e.g., in a Southern or Northern blot). Once the target helicase nucleic acid is identified, it can be isolated according to standard methods known to those of skill in the art (see, e.g., Sambrook et al. (1989) *Molecular Cloning: A Laboratory Manual,* 2nd Ed., Vols. 1–3, Cold Spring Harbor Laboratory; Berger and Kimmel (1987) *Methods in Enzymology,* Vol. 152: *Guide to Molecular Cloning Techniques,* San Diego: Academic Press, Inc.; or Ausubel et al. (1987) *Current Protocols in Molecular Biology,* Greene Publishing and Wiley-Interscience, New York).

Helicases can be expressed in a variety of host cells, including *E. coli,* other bacterial hosts, yeast, and various higher eukaryotic cells, such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. The recombinant protein gene will be operably linked to appropriate expression control sequences for each host. For *E. coli,* this includes a promoter, such as the T7, trp or lambda w promoters, a ribosome binding site and, preferably, a transcription termination signal. For eukaryotic cells, the control sequences will include a promoter and, preferably, an enhancer derived from immunoglobulin genes, SV40, cytomegalovirus, etc., and a polyadenylation sequence. The control sequences may further include splice donor and acceptor sequences.

Expression vectors encoding helicases can be transferred into the chosen host cell by well-known methods, such as calcium chloride transformation for *E. coli* and calcium phosphate treatment or electroporation for mammalian cells. Cells transformed by the vectors can be selected by resistance to antibiotics conferred by genes contained on the vectors, such as the amp, gpt, neo and hyg genes.

Once expressed, the recombinant helicases can be purified according to standard procedures known to those of skill in the art. Such procedures include, but are not limited to, ammonium sulfate precipitation, affinity columns, column chromatography, gel electrophoresis and the like (see, generally, R. Scopes, Protein Purification, Springer—Verlag, N.Y. (1982), Deutscher, *Methods in Enzymology Vol. 182: Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

In some embodiments, only a portion of a native helicase is used in the assays of the present invention, the portion being sufficient for helicase activity of preferably not less than an order of magnitude less than that of the full-length helicases. Portions capable of imparting the requisite binding specificity and affinity are readily identified by those skilled in the art. A wide variety of molecular and biochemical methods are available for generating catalytic fragments of a helicase.

C. Assay Steps and Components

In the initial step of the assays of the present invention, a reaction mixture comprising a first nucleic acid hybridized to a complementary unlabeled second nucleic acid, a helicase polypeptide and a nucleoside triphosphate is incubated under conditions suitable for the helicase polypeptide to unhybridize, i.e., unwind, the first nucleic acid and the second nucleic acid. In a presently preferred embodiment, a potential modulator of helicase activity is also added to the reaction mixture and the effect of the modulator on the helicase activity is determined. As explained in greater detail hereinbelow, virtually any compound can be screened for its ability to modulate helicase activity.

In this step, the hybridized first and second nucleic acids can be RNA or DNA, linear or circular, depending on the specificity of the targeted helicase. In addition, other nucleic acids or structural analogs can be employed in the assays of the present invention so long as they provide an active substrate for the targeted helicase activity. The nucleic acids can be any sequence that provides a convenient substrate for the targeted helicase. DNA duplexes, RNA duplexes and DNA:RNA heteroduplexes can all serve as substrates for the targeted helicase activity (see, e.g., Matson, et al., *Annu. Rev. Biochem.,* 59:289–329 (1990). Moreover, the nucleic acids can be complementary over the entire length of at least one of the nucleic acids or, alternatively, there may be regions of noncomplementarity to the 5' and/or 3' of the complementary region. Introducing these 5' and/or 3' noncomplementary regions provides molecular forks that yield better substrates for some helicases. Moreover, the nucleic acids can be of any length amenable to the assay conditions employed. For example, ensuring helicase substrate specificity and minimizing non-specific renaturation requires a minimal region of complementarity between the first and second nucleic acids, preferably at least about 12, more preferably at least about 18 and even more preferably at least about 24 continuous base pairs.

Generally, conveniently replicated vectors, e.g., phage or restriction fragments thereof, provide an inexpensive source of the nucleic acids. Alternatively, the nucleic acids can be made synthetically. Synthetic nucleic acids are typically synthesized chemically according to common solid phase phosphoramidite triester methods described, for example, by Beaucage and Caruthers, *Tetrahedron Letts.* 22(20):1859–1862 (1981), using, for example, an automated synthesizer as described by Needham-VanDevanter, et al., *Nucleic Acids Res.* 12: 6159–6168 (1984). Nucleic acids can also be custom made and ordered from a variety of commercial sources known to persons of skill. The assays of the present invention are generally compatible with the presence of DNA binding proteins, such as histones. It is often advantageous to include a variety of potential substrates, e.g., double-stranded nucleic acids of varied size, sequence, protein complexing, etc. to improve the likelihood of detecting substrate-sensitive helicases.

Typically, the reaction mixture is incubated under conditions whereby the helicase (or helicases) unhybridizes, i.e., unwinds, the first and second nucleic acids at a first, control helicase activity, thereby converting at least a detectable portion and, preferably, substantially all of the initial amount of hybridized, i.e., double-stranded, nucleic acid into unhybridized complementary single-stranded nucleic acid. As such, a wide variety of reaction conditions can be employed depending on the targeted helicase(s). In vitro conditions to support activity of exemplary helicases are exemplified below and/or otherwise known in the art. For example, the reaction generally requires the presence of an effective amount of a nucleoside triphosphate, such as ATP. For many helicases that are pathogenic in mammals, the reaction is carried out at room or elevated temperatures, usually in the range of 200 to 40° C. and, more preferably, at room temperature (about 25° C.). For high-throughput applications, the reaction time is minimized, and is usually from 0.1 to 4 hours, more usually about 0.5 to 1.5 hours.

In addition to the foregoing, the reaction mixture usually includes additional reagents, such as salts, buffers, etc., to facilitate or maximize helicase activity. Also, reagents that reduce non-specific or background denaturation or otherwise improve the efficiency of the assay, such as protease inhibitors, nuclease inhibitors, antimicrobial agents, single-stranded DNA binding protein, etc., can be used in the assays of the present invention.

Moreover, depending on the method used to detect the presence of the immobilizable hybridization complex on the solid support, the first nucleic acid will generally comprise a detectable label, which label is absent from the second nucleic acid. As explained hereinbelow, a wide variety of directly and/or indirectly detectable labels may be used so long as they are compatible with the assay. Exemplary directly detectable labels include, for example, radiolabels, fluorescent labels, etc.; whereas, exemplary indirectly detectable labels include, for example, epitope tags, biotin, nucleoside analogs, such as digoxigenin, etc.

Following incubation, an excess amount of a third nucleic acid comprising an immobilizable tag is added to the reaction mixture. The third nucleic acid is complementary to the first nucleic acid. Again, the nucleic acids can be complementary over the entire length of at least one of the nucleic acids or, alternatively, there may be noncomplementary regions that are 5' and/or 3' of the complementary region. The third nucleic acid is generally r added in about a 10-fold to about a 500-fold excess and, more preferably, in about a 50-fold to about a 200-fold excess. In a presently preferred embodiment, the third nucleic acid is added in a high salt solution. The final concentration of salt in the reaction mixture is from about 0.25 to about 1.0 M NaCl. Once the third nucleic acid has been added, the reaction mixture is incubated under conditions suitable for the third nucleic acid to hybridize to the first nucleic acid to form an immobilizable hybridization complex.

The immobilizable hybridization complex becomes immobilized on the solid support to which the immobilizable tag binds. As explained hereinbelow, numerous solid supports and immobilizable tags can be used in the assays of the present invention. The immobilization of the hybridization complex on the solid support can be, for example, direct (substrate-hybridization complex) or indirect via a ligand (substrate-ligand-hybridization complex) or ligand receptor complex (substrate-receptor-ligand-hybridization complex), etc. Generally, to avoid interference, any selected immobilizable tag on the third nucleic acid should not be identical to any selected label or detectable moiety on the first nucleic acid. Moreover, depending on the selected immobilization or capture mechanism employed, the reaction mixture may be supplemented with a suitable pH buffer and salt to ensure that the ionic strength and pH of the mixture is conducive to optimal binding. For high-throughput applications, the immobilization or capture step is generally less than 4 hours, preferably less than 2 hours and more preferably less than about 1 hour. Typically, the immobilization or capture step is most conveniently carried out at room temperature.

Following immobilization, the solid support is washed and, thereafter, the presence, absence or amount of the immobilizable hybridization complex on the solid support is determined either directly or indirectly. Most typically, helicase activity is measured by quantitating the amount of label or detectable moiety fixed on the solid support by the capture of the immobilizable hybridization complex that occurs when helicase activity is present. Typically, the presence in the reaction mixture of a modulator that inhibits helicase activity will decrease the amount of label fixed to the solid support relative to a control reaction which does not comprise the modulator, or as compared to a baseline established for a particular lot of helicase. As explained hereinbelow, numerous labels and means of detecting and quantitating labels are well known to those of skill in the art. Thus, for example, where the label is a radioactive label, means for detection include a scintillation counter or photographic film as in autoradiography. Moreover, where the label is optically detectable, typical detectors include microscopes, cameras, phototubes and photodiodes and other detection systems that are widely available.

D. Immobilizable Tags

In the assays of the present invention, the immobilizable hybridization complex is immobilized on a solid support. Typically, the third nucleic acid, which is complementary to the first nucleic acid, contains an immobilizable tag. The immobilizable tag can be any of a variety of components. In one embodiment, the immobilizable tag is immobilized, i.e., binds, directly to the solid support. In an alternative embodiment, a molecule that binds the immobilizable tag (i.e., a capture moiety or tag binder) is fixed to a solid support, and the immobilizable hybridization complex is immobilized on the solid support as a result of the interaction between the immobilizable tag and the capture moiety.

Preferably, those of skill in the art will readily appreciate that a number of immobilizable tags and capture moieties can be used that are based upon numerous molecular interactions well described in the literature. For instance, where an immobilizable tag has a natural binder (e.g., biotin, protein A or protein G), it can be used in conjunction with an appropriate capture moiety (e.g., avidin, streptavidin, neutravidin, the Fc region of an immunoglobulin, etc.). Moreover, antibodies to molecules having natural capture moieties, such as biotin, are also widely available as appropriate capture moiety or tag binders (see, SIGMA Immunochemicals 1998 catalogue, SIGMA Chemical Co. (St. Louis Mo.)).

Similarly, any haptenic or antigenic compound can be used in combination with an appropriate antibody to form an immobilizable tag/capture moiety pair. Thousands of specific antibodies are readily available from a number of commercial sources and many additional antibodies are described in the literature (see, SIGMA's catalogue, supra). In fact, the antibody can serve as either the immobilizable tag binder or, in an indirect immobilization assay format, as the capture moiety. In one common indirect immobilization configuration, the capture moiety is a first antibody that recognizes the immobilizable tag and the solid support has bound thereto a second antibody that recognizes the first antibody. In addition to antibody-antigen interactions, receptor-ligand interactions are also appropriate as immobilizable tag and capture moiety pairs. For example, agonists and antagonists of cell membrane receptors can be used in forming immobilizable tag and capture moiety pairs. For instance, cell receptor-ligand interactions, such as transferrin, c-kit, viral receptor ligands, cytokine receptors, chemokine receptors, interleukin receptors, immunoglobulin receptors and antibodies, the cadherein family, the integrin family, the selectin family, can all be employed in the methods of the present invention (see, e.g., Pigott and Power (1993), *The Adhesion Molecule FactsBook* (Academic Press New York, and Hulme (ed.)), *Receptor Ligand Interactions: A Practical Approach*, (Rickwood and Hames (series editors) Hulme (ed.) IRL Press at Oxford Press NY). Similarly, toxins, venoms, viral epitopes, hormones (e.g., opiates, steroids, etc.), intracellular receptors (e.g., receptors which mediate the effects of various small ligands, including steroids, thyroid hormone, retinoids and vitamin D, peptides), drugs, lectins, sugars, nucleic acids (both linear and cyclic polymer configurations), oligosaccharides, proteins, phospholipids and antibodies can all interact with various cell receptors.

Synthetic polymers, such as heteropolymers, in which a known drug is covalently bound to any of the above can also form appropriate immobilizable tags or capture moieties. Such polymers include, but are not limited to, polyurethanes, polyesters, polycarbonates, polyureas, polyamides, polyethyleneimines, polyarylene sulfides, polysiloxanes, polyimides, and polyacetates. Numerous other immobilizable tag/capture moiety pairs that are useful in assay systems described herein will be readily apparent to those of skill in the art upon review of this disclosure.

Specific immobilizable tag-capture moiety interactions will occur when the immobilizable tag and capture moiety bind with a KD of at least about 0.01 $\mu$M, preferably, at least about 0.001 $\mu$M or better and, most typically and preferably, 0.0001 $\mu$M or better under standard assay conditions.

Attachment of the third nucleic acid to the various immobilizable tags is carried out using conventional methods and procedures know to and used by those of skill in the art. In one embodiment, a linker is added to the third nucleic acid and attachment to the immobilizable tag is carried out through the use of the linker. Suitable linkers include, but are not limited to, proteins, carbohydrates, lipids, peptides, polyesters, nucleic acids and synthetic polymers. Common linkers include polypeptide sequences, such as poly-gly sequences of between about 5 and 200 amino acids. In some embodiments, proline residues are incorporated into the linker to prevent the formation of significant secondary structural elements by the linker. Flexible linkers suitable for use in the present invention are known to persons of skill in the art. For example, poly(ethylene glycol) linkers are available from Shearwater Polymers, Inc. (Huntsville, Ala.). These linkers optionally have amide linkages, sulfhydryl linkages, or heterobifunctional linkages. The immobilizable tag should be attached in a manner that does not interfere with the ability of the third nucleic acid to hybridize with the first nucleic acid.

Capture moieties or tag binders are fixed to solid substrates using any of a variety of methods currently available. Solid substrates are commonly derivatized or functionalized by exposing all or a portion of the substrate to a chemical reagent that fixes a chemical group to the surface which is reactive with a portion of the capture moiety. For example, groups that are suitable for attachment to a longer chain portion include, but are not limited to, amine, hydroxyl, thiol and carboxyl groups. Aminoalkylsilanes and hydroxyalkylsilanes can be used to functionalize a variety of surfaces, such as a glass surface. The construction of such solid phase biopolymer arrays is well described in the literature (see, e.g., Merrifield, *J. Am. Chem. Soc.,* 85:2149–2154 (1963) (describing solid phase synthesis of, e.g., peptides); Geysen, et al., *J. Immun. Meth.,* 102:259–274 (1987) (describing synthesis of solid phase components on pins); Frank and Doring, *Tetrahedron,* 44:6031–6040 (1988) (describing synthesis of various peptide sequences on cellulose disks); Fodor, et al., *Science,* 251:767–777 (1991); Sheldon, et al., *Clinical Chemistry* 39(4):718–719 (1993); and Kozal, et al., *Nature Medicine,* 2(7):753–759 (1996) (all describing arrays of biopolymers fixed to solid substrates). Non-chemical approaches for fixing capture moieties to substrates include commonly used methods, such as heat, cross-linking by UV radiation, and the like.

In the assays of the present invention, the immobilizable hybridization complex is immobilized on or bound to a solid support or solid phase. Typically, the solid support is a matrix of material in a substantially fixed arrangement (i.e., an insoluble polymeric material, inorganic or organic matrix, gel, aggregate, precipitate or resin). Solid supports can be flat or planar, or can have substantially different conformations. For example, the substrate can exist as particles, beads, strands, precipitates, gels, sheets, tubing, spheres, containers, capillaries, pads, slices, films, plates, slides, etc. Preferred solid supports in accordance with the present invention include, but are not limited to, the following: cellulose, agarose, dextran, polyacrylate, polyacrylamide, polystyrene, polyvinyl chloride, or their derivatives, chitin, sepharose, oxirane substituted acrylic beads, starch, oxidized starch (i.e., polymeric dialdehyde), collagen, keratin, elastin, bovine hide powder, bacterial cell wall peptidoglycan or fragments thereof, diazotized paper, nylon, polyethylene terephthalates, polycarbonates, metallic particles and controlled pore glass. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham, Mass.), Ciba Coming (Medfield, Mass.), Bangs Laboratories (Carmel, Ind.), and BioQuest, Inc. (Atkinson, N.H.). Of these, certain solid supports are presently preferred, namely, cellulose and cellulose derivatives (e.g., nitrocellulose), agarose, dextran, polyacrylate, polyacrylamide, polystyrene, polyvinyl chloride and glass. Even more preferred for use as a solid support are nitrocellulose, polystyrene and polyvinyl chloride. Polystyrene and polyvinyl chloride are normally used as microtiter plates, while nitrocellulose is normally used in sheets.

Once the immobilized hybridization complex is fixed, i.e., immobilized, on the solid support, the solid support is washed to remove non-immobilized components. Wash conditions are selected so that the immobilizable hybridization complex remains bound to the solid support or any capture moieties. Preferably, the solid support is washed with water. Other suitable wash solutions, such as buffered solutions, are known to those of skill in the art. One or more washes can be employed. In preferred embodiments, washes are repeated until a signal to noise ratio of 2x–10x (or higher) is achieved, i.e., until at least about 50–90% of the unattached nucleic acid and helicase is removed from the solid support, and often until at least 90–95% is removed. The determination of how much hybridization complex is bound to the solid support can be done by performing a calibration of the assay, i.e., by performing the helicase assay in the absence of a modulator and then repeatedly washing the solid support to determine the amount of the hybridization complex bound to the solid support, and the number of washes required to remove unbound nucleic acids and helicase.

E. Labeling Strategies

As discussed above, the immobilizable hybridization complex must be capable of being detected directly or indirectly. In a presently preferred embodiment, the first nucleic acid comprises a label or detectable moiety. The detectable labels used in the present invention can be primary labels (where the label comprises an element that is detected directly or that produces a directly detectable element) or, alternatively, they can be secondary labels (where the detected label binds to a primary label, e.g., as is commonly used in immunological labeling). An introduction to labels, labeling procedures and detection of labels is found in Polak and Van Noorden, *Introduction to Immunocytochemistry* (2nd ed., Springer Verlag, N.Y. (1997)); and in Haugland, *Handbook of Fluorescent Probes and Research Chemicals,* a combined handbook and catalogue Published by Molecular Probes, Inc. (Eugene, Oreg. (1996)). Primary and secondary labels can include undetected elements as well as detected elements. Primary and secondary labels useful in the present invention include, but are not limited to, spectral labels, such as fluorescent dyes (e.g., fluorescein and derivatives, such as fluorescein isothiocyanate (FITC) and Oregon Green™; rhodamine and derivatives, such Texas red, tetrarhodimine isothiocynate (TRITC), etc., digoxigenin, biotin, phycoerythrin, AMCA, CyDyes™, and the like; radiolabels, such as $^3H$, $^{125}I$, $^{35}S$, $^{14}C$, $^{32}P$, $^{33}P$, etc.; enzymes, such as horse radish peroxidase, alkaline phosphatase, etc.; spectral colorimetric labels, such as colloidal gold or colored glass or plastic beads, such as polystyrene, polypropylene, latex, etc. The label can be coupled directly or indirectly to a component of the detection assay (e.g., the first nucleic acid) using methods well known in the art. As indicated above, a wide variety of labels can be used, with the choice of label depending on sensitivity required, ease of conjugation with, for example, the first nucleic acid, stability requirements, and available instrumentation and disposal provisions.

Preferred labels include those that use: 1) chemiluminescence (using horseradish peroxidase and/or alkaline phosphatase with substrates that produce photons as breakdown products as described above), with kits being available from, for example, Molecular Probes, Amersham, Boehringer-Mannheim, and Life Technologies/Gibco BRL; 2) color production (using horseradish peroxidase and/or alkaline phosphatase with substrates that produce a colored precipitate), with kits being available from Life Technologies/Gibco BRL, and Boehringer-Mannheim; 3) hemifluorescence (using, for example, alkaline phosphatase and the substrate AttoPhos [Amersham] or other substrates that produce fluorescent products), 4) fluorescence (e.g., using Cy-5 [Amersham]), fluorescein, and other fluorescent tags); and 5) radioactivity. Other methods for labeling and detection will be readily apparent to one skilled in the art.

Preferred enzymes that can be conjugated to the detection moieties of the invention include, but are not limited to, β-galactosidase, luciferase, horse radish peroxidase and alkaline phosphatase. The chemiluminescent substrate for luciferase is luciferin. One example of a chemiluminescent substrate for β-galactosidase is 4-methylumbelliferyl-β-D-galactoside. Examples of alkaline phosphatase substrates include p-nitrophenyl phosphate (pNPP), which is detected using a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3, 2'-adamantane], which is detected using a luminometer. Examples of horseradish peroxidase substrates include 2,2'azino-bis(3-ethylbenzthiazoline-6 sulfonic acid) (ABTS), 5-aminosalicylic acid (SAS), o-dianisidine, and o-phenylenediamine (OPD), which are detected using a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4CIN), which are detected visually. Other suitable substrates are known to those skilled in the art. The enzyme-substrate reaction and product detection are performed according to standard procedures known to those skilled in the art and kits for performing enzyme immunoassays are available as described above.

Most typically, helicase activity is measured by quantitating the amount of label fixed to the solid support by binding of the detection moieties. Typically, presence of a modulator during incubation will increase or decrease the amount of label fixed to the solid support relative to a control incubation which does not comprise the modulator, or as compared to a baseline established for a particular reaction type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems that are widely available.

In general, a detector which monitors a particular probe or probe combination is used to detect the label. Typical detectors include, but are not limited to, spectrophotometers, phototubes and photodiodes, microscopes, scintillation counters, cameras, film and the like, as well as combinations thereof Examples of suitable detectors are widely available from a variety of commercial sources known to persons of skill.

F. Modulators

The invention also provides methods of identifying compounds that modulate helicase activity. Essentially any chemical compound can be used as a potential activity modulator in the assays of the invention, although most often compounds that can be dissolved in aqueous or organic (especially DMSO-based) solutions are used. The assays are designed to screen large chemical libraries by automating the assay steps and providing compounds from any convenient source to assay, which are typically run in parallel (e.g., in microtiter formats on microtiter plates in robotic assays). It will be appreciated by those of skill in the art that there are many commercial suppliers of chemical compounds, including Sigma Chemical Co. (St. Louis, Mo.), Aldrich Chemical Co. (St. Louis, Mo.), Sigma-Aldrich (St. Louis, Mo.), Fluka Chemika-Biochemica Analytika (Buchs Switzerland), and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, erg., U.S. Pat. No. 5,010,175, Furka, *Int. J. Pept. Prot. Res.,* 37:487–493 (1991) and Houghton, et al., *Nature,* 354:84–88 (1991)). Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA,* 90:6909–6913 (1993)); vinylogous polypeptides (Hagihara, etal., *J. Amer. Chem. Soc.* 114:6568 (1992)); nonpeptidal peptidomimetics with β-D-glucose scaffolding (Hirschmann, et al., *J. Amer. Chem. Soc.,* 114:9217–9218 (1992)); analogous organic syntheses of small compound libraries (Chen, et al., *J. Amer. Chem. Soc.,* 116:2661 (1994)); oligocarbamates (Cho, et al., *Science,* 261:1303 (1993)); and/or peptidyl phosphonates (Campbell, et al.,*J. Org. Chem.* 59:658 (1994)); nucleic acid libraries (see, Ausubel, Berger and Sambrook, all supra); peptide nucleic acid libraries (see, e.g., U.S. Pat. No. 5,539, 083); antibody libraries (see, e.g., Vaughn, et al., *Nature Biotechnology,* 14(3):309–314 (1996) and PCT/US96/10287); carbohydrate libraries (see, e.g., Liang, et al., *Science,* 274:1520–1522 (1996) and U.S. Pat. No. 5,593, 853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

As noted, the invention provides in vitro assays for helicase activity in a high-throughput format. Control reactions that measure helicase activity in a reaction that does not include a helicase activity modulator are optional, as the assays are highly uniform. However, such optional control reactions are appropriate and increase the reliability of the assay. Accordingly, in a preferred embodiment, the methods of the invention include such a control reaction.

In some assays, it will be desirable to have positive controls to ensure that the components of the assays are working properly. At least two types of positive controls are appropriate. First, a known activator of helicase activity can be incubated with one sample of the assay, and the resulting increase in helicase activity determined according to the methods herein. Second, a known inhibitor of helicase activity can be added, and the resulting decrease helicase activity similarly detected. It will be appreciated that modulators can also be combined with helicase activators or inhibitors to find modulators that inhibit helicase activation or repression that is otherwise caused by the presence of the known helicase activity modulator.

In the high throughput assays of the invention, it is possible to screen up to several thousand different modulators in a single day. In particular, each well of a microtiter plate can be used to run a separate assay against a selected potential modulator, or if concentration or incubation time effects are to be observed, every 5–10 wells can test a single modulator. Thus, a single standard microtiter plate can assay about 100 (96) modulators. If 1536 well plates are used, then a single plate can easily assay from about 100- about 1500 different compounds. It is possible to assay many different plates per day; assay screens for up to about 6,000–20,000, and even up to about 100,000–1,000,000 different compounds is possible using the integrated systems of the invention.

G. Compositions, Kits and Integrated Systems

The invention provides compositions, kits and integrated systems for practicing the assays described herein. For example, an assay composition having a labeled first nucleic acid, a second nucleic acid that can be hybridize to the first nucleic acid, a helicase polypeptide and a third nucleic acid that can also hybridize to the first nucleic acid and which comprises an immobilizable tag is provided by the present invention. Additional assay components as described above are also provided. For instance, a solid support or substrate to which the tagged hybridization complex, if formed, can be bound can also be included. Such solid supports include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The invention also provides kits for practicing the helicase screening assays described above. The kits can include any of the compositions noted above, and optionally further include additional components such as instructions to practice a high-throughput method of screening for a helicase activity modulator, one or more containers or compartments (e.g., to hold the helicase, the first nucleic acid, the second nucleic acid, the third nucleic acid, modulators, or the like), a control activity modulator, a robotic armature for mixing kit components, and the like.

The invention also provides integrated systems for high throughput screening of potential modulators of helicase activity. Such systems typically include a robotic armature which transfers fluid from a source to a destination, a controller which controls the robotic armature, a label detector, a data storage unit which records label detection, and an assay component such as a microtiter dish comprising a well having a capture moiety for an immobilizable hybridization complex affixed to the well.

A number of well-known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate 11, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art.

Any of the assays for compounds that modulate helicase activity, as described herein, are amenable to high throughput screening. High throughput screening systems are commercially available (see, e.g., Zymark Corp. (Hopkinton, Mass.); Air Technical Industries (Mentor, Ohio); Beckman Instruments, Inc. (Fullerton, Calif.); Precision Systems, Inc., (Natick, Mass.), etc.). Such systems typically automate entire procedures including all sample and reagent pipetting, liquid dispensing, timed incubations, and final readings of the microplate in detector(s) appropriate for the assay. These configurable systems provide high-throughput and rapid start up as well as a high degree of flexibility and customization. The manufacturers of such systems provide detailed protocols for the various high throughput systems.

Optical images viewed (and, optionally, recorded) by a camera or other recording device (e.g., a photodiode and data storage device) are optionally further processed in any of the embodiments described herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

The invention will be described in greater detail by way of specific examples. The following examples are offered for illustrative purposes, and are not intended to limit the invention in any manner. Those of skill in the art will readily recognize a variety of noncritical parameters that can be changed or modified to yield essentially the same results.

EXAMPLES

This example illustrates a NS3 chemiluminescent assay of an NS3 helicase according to the present invention. This example is provided by way of illustration and not by way of limitation; one of skill will recognize a variety of substitutions that can be made upon complete review of this disclosure.

1. Materials a. Assay Buffer: 25 mM MOPS (p14 6.8), 50 µg/ml BSA, 4 mM $MgCl_2$, 5% glycerol, 2 mM DTT.

b. Annealed Substrate NSDNAB-Fl Oligo

```
5'-GGA CTC TCT CAA GCA GCA GCA AGC GGT CCA CGC TGG TTT GTT TTT TTT TTT TTT T-
Fluorescein(SEQ ID NO:1)
```

NSDNABr Oligo

```
5'-TTT TTT TTT TTT TTC AAA CCA GCG TGG ACC GCT TGC TGC AAC TCT CTC AGG(SEQ ID NO:2)
```

All of the oligos were diluted to 100 pmole/µl in TE buffer. Mix 10 µl of NSDNAB-Fl+40 µl of NSDNABr+0.5 µl of 5 M NaCl. Heat the mixture to 95° C. for 5 min. and cool slowly to RT (place heating block at RT).

c. Capture Oligo: NSDNABr-Bio

```
5'-Biotin TTT TTT TTT TTT TTC AAA CCA GCG TGG ACC GCT TGC TGC AAC TCT CTC AGG(SEQ ID NO:3)
```

The capture oligo was diluted to 100 pmoles/µl in TE buffer.

d. Capture buffer:

The capture buffer is 20×SSC; 5 M NaCl. The capture oligo is diluted to 0.2 pmoles/µl in the capture buffer.

e. HRP antibody dilution buffer:

The HRP antibody dillution buffer is 25 mM Hepes, 0.5 M NaCl, 0.1% BSA.

2. Assay Steps

The NS3 chemiluminescent assay is performed on neutravidin coated plates, which are commercially available from Pierce Chemicals (Rockford, Ill.).

1. 5 mM ATP is added to 70 µl assay buffer.
  2. 10 µl DMSO is added to the assay buffer.
  3. The annealed flourescein oligo (1/10,000 of above stock 20 femtomoles/reaction) and NS3 protein (5 ng) are added to 20 µl assay buffer (without ATP).
  4. The reaction mixture is incubated for about 1 hr at RT.
  5. 10 µl of the biotinylated oligo (2 picomoles/reaction) is added to the reaction mixture.
  6. The reaction mixture is incubated for about 30 min. at RT.
  7. The solid support is washed 5× with water.
  8. 100 µl of Anti-Fl Antibody (BM Cat # 1426346) is added to the solid support. 150 U of the lyophilized antibody is dissolved in water, this stock solution is dissolved 1/5000 in HRP dilution buffer and 100 μl of this is delivered to each well.

9. The reaction mixture is incubated for about 45 min. at RT.
10. The solid support is washed 5× with water.
11. 100 μl of super signal HRP substrate from Pierce Chemicals is added to the solid support.
12. The read-out is chemiluminescence.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for determining helicase activity, said method comprising:

incubating a reaction mixture comprising a first nucleic acid hybridized to a complementary unlabeled second nucleic acid, a helicase polypeptide and a nucleoside triphosphate under conditions suitable for said helicase polypeptide to unhybridize said first nucleic acid and said second nucleic acid;

adding an excess of a third nucleic acid comprising an immobilizable tag to said reaction mixture, wherein said third nucleic acid is complementary to said first nucleic acid;

incubating said reaction mixture under conditions suitable for said third nucleic acid to hybridize to said first nucleic acid to form an immobilizable hybridization complex, whereby said immobilizable hybridization complex is immobilized on a solid support; and detecting the presence of said immobilizable hybridization complex on said solid support.

2. The method of claim 1, wherein said immobilizable tag binds to said solid support directly.

3. The method of claim 1, wherein said immobilizable tag binds to said solid support indirectly.

4. The method of claim 1, wherein said immobilizable complex is directly detected.

5. The method of claim 1, wherein said immobilizable complex is directly detected through the use of a label on said first nucleic acid.

6. The method of claim 1, wherein said immobilizable complex is indirectly detected.

7. The method of claim 1, wherein said helicase polypeptide is a full-length helicase.

8. The method of claim 1, wherein said helicase polypeptide is from a pathogenic organism.

9. The method of claim 1, wherein said helicase polypeptide is a fungal helicase polypeptide.

10. The method of claim 1, wherein said helicase polypeptide is a bacterial helicase polypeptide.

11. The method of claim 1, wherein said helicase polypeptide is a viral helicase polypeptide.

12. The method of claim 1, wherein said helicase polypeptide is a human helicase polypeptide.

13. The method of claim 1, wherein said reaction mixture further comprises a potential modulator of helicase activity.

14. The method of claim 1, further comprising quantitating the amount of said immobilizable hybridization complex bound to said solid support.

15. The method of claim 1, wherein said first nucleic acid and said second nucleic acid comprise regions that are noncomplementary.

16. The method of claim 1, wherein said first nucleic acid and said second nucleic acid are both DNA.

17. The method of claim 1, wherein said first nucleic acid and said second nucleic acid are both RNA.

18. The method of claim 1, wherein said third nucleic acid is added in a high salt solution resulting in a final salt concentration for the reaction mixture of from about 0.25 M to about 1.0 M.

19. The method of claim 1, wherein said solid support comprises a substrate coated with streptavidin or neutravidin and the immobilizable tag comprises a biotin moiety.

20. A method of identifying a modulator of helicase activity, said method comprising:

incubating a reaction mixture comprising a first nucleic acid hybridized to a complementary unlabeled second nucleic acid, a helicase polypeptide, and a nucleoside triphosphate under conditions suitable for said helicase polypeptide to unhybridize said first nucleic acid and said second nucleic acid;

adding an excess of a third nucleic acid comprising an immobilizable tag to said reaction mixture, wherein said third nucleic acid is complementary to said first nucleic acid;

incubating said reaction mixture under conditions suitable for said third nucleic acid to hybridize to said labeled first nucleic acid to form an immobilizable hybridization complex, whereby said immobilizable hybridization complex is immobilized on a solid support; and determining the helicase activity in the presence and absence of a potential modulator, wherein said potential modulator increases or decreases helicase activity, thereby identifying a modulator of helicase activity.

* * * * *

SEQUENCE LISTING

```
<160> NUMBER OF SEQ ID NOS: 3

<210> SEQ ID NO 1
<211> LENGTH: 55
<212> TYPE: DNA
<213> ORGANISM: Artificial Sequence
<220> FEATURE:
<223> OTHER INFORMATION: Description of Artificial Sequence:annealed
      substrate NSDNAB-Fl oligo
<220> FEATURE:
<221> NAME/KEY: modified_base
<222> LOCATION: (55)
<223> OTHER INFORMATION: n = t-flourescein

<400> SEQUENCE: 1
ggactctctc aagcagcaag cggtccacgc tggtttgttt tttttttttt ttttn           55

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:annealed
      substrate NSDNABr oligo

<400> SEQUENCE: 2
tttttttttt ttttcaaacc agcgtggacc gcttgctgca actctctcag g              51

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence:capture
      oligo NSDNABr-Bio
<220> FEATURE:
<221> NAME/KEY: modified_base
<222> LOCATION: (1)
<223> OTHER INFORMATION: n = 5'-biotinylated t

<400> SEQUENCE: 3 ntttttttttt ttttcaaacc agcgtggacc gcttgctgca actctctcag g             51
```